United States Patent [19]
Haight et al.

[11] Patent Number: 5,932,766
[45] Date of Patent: Aug. 3, 1999

[54] PROCESS FOR THE PREPARATION OF SUBSTITUTED KETO-ENAMINES

[75] Inventors: Anthony R. Haight, Wadsworth, Ill.; Timothy L. Stuk, Holland, Mich.; Jerome A. Menzia, New Berlin, Wis.

[73] Assignee: Abbott Laboratories, Abbott Park, Ill.

[21] Appl. No.: 08/862,951

[22] Filed: May 30, 1997

[51] Int. Cl.$^6$ ...................... C07C 211/22; C07C 211/28; C07C 255/00
[52] U.S. Cl. .................... 564/372; 546/99; 548/482; 558/388; 558/404; 558/408; 558/311; 564/342; 564/343
[58] Field of Search ................ 546/99; 548/482; 558/388, 404, 408; 564/342, 343, 372

[56] References Cited

U.S. PATENT DOCUMENTS

| | | | |
|---|---|---|---|
| 5,491,253 | 2/1996 | Stuk et al. | 560/27 |
| 5,541,206 | 7/1996 | Kempf et al. | 514/365 |
| 5,688,985 | 11/1997 | Fujihara | 558/311 |

FOREIGN PATENT DOCUMENTS 0729941  4/1996  European Pat. Off. .

OTHER PUBLICATIONS

Stuk et al., J. Org. Chem. 59 4040–4041 (1994).
Brillon, et al., J. Org. Chem 57 1838–1842 (1992).
Ghosh et al., J. Org. Chem 58 1025–1029 (1993).

*Primary Examiner*—Evelyn Mei Huang
*Attorney, Agent, or Firm*—Steven R. Crowley

[57] ABSTRACT

The present invention discloses a process for the preparation of a compound having formula 4:

The process comprises the step of reacting an enolate having the formula:

with a Grignard reagent. The enolate salt is formed in situ from the reaction of a protected ester wherein M is an alkali metal. $R_6$ and $R_7$ are each hydrogen or are independently selected from (i)

wherein $R_a$ and $R_b$ are independently selected from hydrogen, lower alkyl and phenyl and $R_c$, $R_d$ and $R_e$ are independently selected from hydrogen, lower alkyl, trifluoromethyl, alkoxy, halo and phenyl; and (ii)

wherein the naphthyl ring is unsubstituted or substituted with one, two or three substitutents independently selected from lower alkyl, trifluoromethyl, alkoxy and halo. Alternatively, $R_6$ is as defined above and $R_7$ is $R_{12}OC(O)$— wherein $R_{12}$ is benzyl; or $R_6$ and $R_7$ taken together with the nitrogen atom to which they are bonded form wherein $R_f$, $R_g$, $R_h$ and $R_i$ are independently selected from hydrogen, lower alkyl, alkoxy, halogen and trifluoromethyl.

22 Claims, No Drawings

PROCESS FOR THE PREPARATION OF SUBSTITUTED KETO-ENAMINES

TECHNICAL FIELD

The present invention relates to a process for the preparation of an enamine intermediate which is useful for the preparation of substituted 2,5-diamino-3-hydroxyhexanes.

BACKGROUND OF THE INVENTION

Compounds which are inhibitors of human immunodeficiency virus (HIV) protease are useful for inhibiting HIV protease in vitro and in vivo and are useful for inhibiting an HIV infection. Certain HIV protease inhibitors comprise a moiety which is a substituted 2,5-diamino-3-hydroxyhexane. HIV protease inhibitors of particular interest are compounds having formula 1:

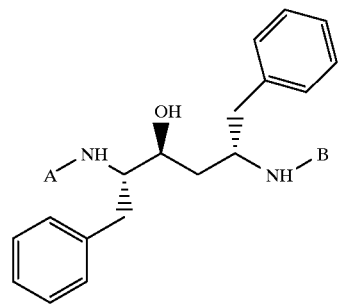

wherein A is $R_2NHCH(R_1)C(O)-$ and B is $R_{2a}$ or wherein A is $R_{2a}$ and B is $R_2NHCH(R_1)C(O)-$ wherein $R_1$ is lower alkyl and $R_2$ and $R_{2a}$ are independently selected from $-C(O)-R_3-R_4$ wherein at each occurrence $R_3$ is independently selected from O, S and $-N(R_5)-$ wherein $R_5$ is hydrogen or lower alkyl and at each occurrence $R_4$ is independently selected from heterocyclic or (heterocyclic)alkyl; or a pharmaceutically acceptable salt, prodrug or ester thereof. Compounds of formula 1 are disclosed in U.S. Pat. No. 5,354,866, issued Oct. 11, 1994, U.S. Pat. No. 5,541,206, issued Jul. 30, 1996, and U.S. Pat. No. 5,491,253, issued Feb. 13, 1996.

A preferred HIV protease inhibitor having formula 1 is a compound of formula 2a:

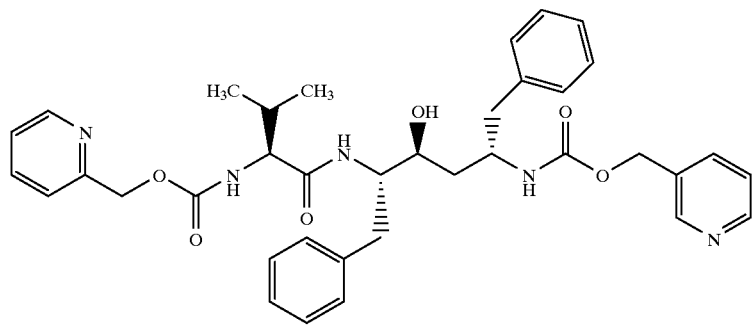

or a pharmaceutically acceptable salt, prodrug or ester thereof.

Another preferred HIV protease inhibitor of formula 1 is a compound of formula 2b:

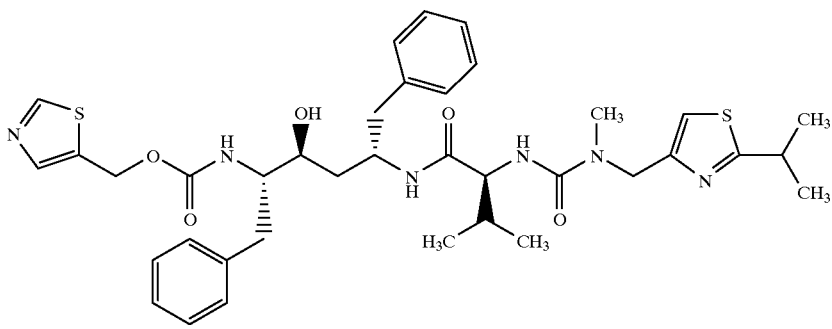

The compound having formula 2b is disclosed in U.S. Pat. No. 5,421,206, issued Jul. 30, 1996.

An intermediate which is especially useful for preparing compounds having formula 1 and 2 is a substantially pure compound having the formula 3:

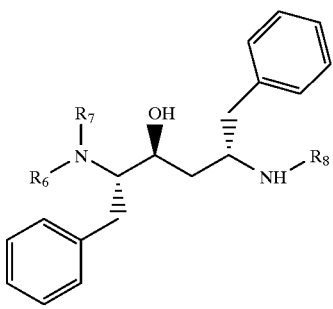

3 wherein $R_6$, $R_7$ and $R_8$ are independently selected from hydrogen and N-protecting groups, such as, for example, t-butyloxycarbonyl (Boc), benzyl and the like; or an acid addition salt thereof. The preparation of compounds having formula 3 has been disclosed in U.S. Pat. No. 5,491,253, issued Feb. 13, 1996 (the '253 patent).

The procedure disclosed in the '253 patent starts with a protected L-phenylalanine benzyl ester. The ester is reacted with an (α-carbanion of acetonitrile in an inert solvent to provide a ketonitrile, shown below.

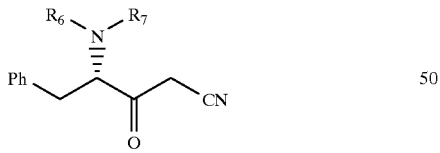

Reaction of the ketonitrile with a benzyl Grignard, usually more than about 3 equivalents, provides the enamine product. The enamine can be readily transformed into compound 3.

An object of the present invention is to provide a simple method for the preparation of enamines which can be converted into diaminols having formula 3.

An object of the present invention is to provide a method for the preparation of enamines which provides the enamines in high yield.

SUMMARY OF THE INVENTION

The present invention discloses a process for the preparation of a compound having formula 4:

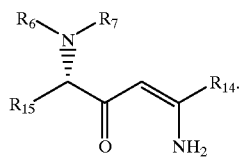

4

The process comprises the step of reacting an enolate having the formula:

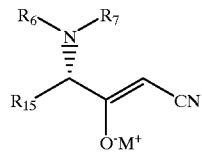

with a Grignard reagent. The enolate salt is formed in situ from a protected ester with a metal amide, $MNH_2$, where M is a metal cation. $R_6$ and $R_7$ are each hydrogen or are independently selected from

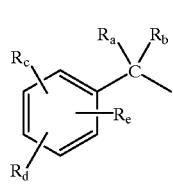

(i)

wherein $R_a$ and $R_b$ are independently selected from hydrogen, lower alkyl and phenyl and $R_c$, $R_d$ and $R_e$ are independently selected from hydrogen, lower alkyl, trifluoromethyl, alkoxy, halo and phenyl; and

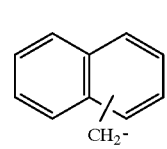

(ii)

wherein the naphthyl ring is unsubstituted or substituted with one, two or three substitutents independently selected from lower alkyl, trifluoromethyl, alkoxy and halo. Alternatively, $R_6$ is as defined above and $R_7$ is $R_{12}OC(O)$— wherein $R_{12}$ is benzyl; or $R_6$ and $R_7$ taken together with the nitrogen atom to which they are bonded form

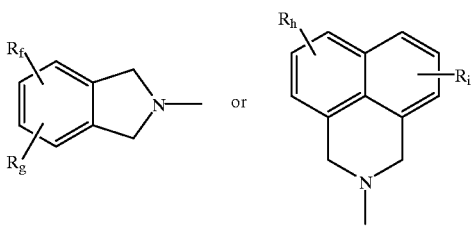

wherein $R_f$, $R_g$, $R_h$ and $R_i$ are independently selected from hydrogen, lower alkyl, alkoxy, halogen and trifluoromethyl with the proviso that $R_6$ and $R_7$ cannot both be hydrogen.

$R_{14}$ is a hydrocarbyl group capable of forming a Grignard reagent. The preferred $R_{14}$ groups are selected from the group consisting of alkyl, substituted alkyl, alkaryl, such as, benzyl, and substituted benzyl, aryl, such as, phenyl, substituted phenyl, naphthyl and substituted naphthyl. $R_{15}$ is selected from the group consisting of hydrogen, alkyl, substituted alkyl, alkaryl, such as, benzyl, and substituted benzyl, aryl, such as, phenyl, substituted phenyl, naphthyl and substituted naphthyl. The process of the invention also includes the preparation of acid addition salts of compound 4.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

The present invention relates to a process for the preparation of a compound having formula 4.

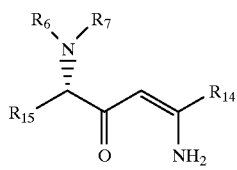

In the process of the invention $R_6$ and $R_7$ are hydrogen or are independently selected from

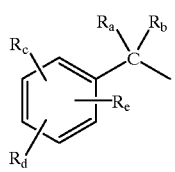

wherein $R_a$ and $R_b$ are independently selected from hydrogen, lower alkyl and phenyl and $R_c$, $R_d$ and $R_e$ are independently selected from hydrogen, lower alkyl, trifluoromethyl, alkoxy, halo, and phenyl; and

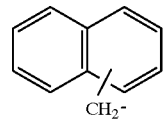

wherein the naphthyl ring is unsubstituted or substituted with one, two or three substitutents independently selected from lower alkyl, trifluoromethyl, alkoxy, and halo; or $R_6$ is as defined above and $R_7$ is $R_{7a}OC(O)$— wherein $R_{7a}$ is lower alkyl or benzyl; or $R_6$ and $R_7$ taken together with the nitrogen atom to which they are bonded are

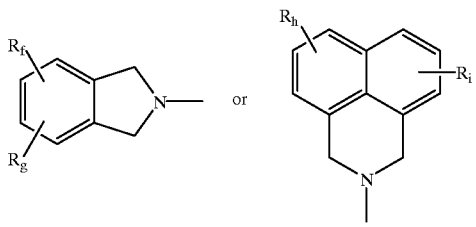

wherein $R_f$, $R_g$, $R_h$ and $R_i$ are independently selected from hydrogen, lower alkyl, alkoxy, halogen, and trifluoromethyl; with the proviso that $R_6$ and $R_7$ cannot both be hydrogen.

$R_{14}$ is a hydrocarbyl group capable of forming a Grignard reagent. The preferred $R_{14}$ groups are selected from the group consisting of alkyl, substituted alkyl, alkaryl, such as, benzyl, and substituted benzyl, aryl, such as, phenyl, substituted phenyl, naphthyl and substituted naphthyl.

$R_{15}$ is selected from the group consisting of hydrogen, alkyl, substituted alkyl, alkaryl, such as, benzyl, and substituted benzyl, aryl, such as, phenyl, substituted phenyl, naphthyl and substituted naphthyl. The process of the invention also includes the preparation of acid addition salts of compound 4.

Examples of suitable substituents for substitution on the alkyl, phenyl, benzyl, and naphthyl groups include but are not limited to lower alkyl, aryl, cycloalkyl, alkoxy, alkoxyalkoxy, thioalkoxy, amino, alkylamino, dialkylamino, arylamino, diarylamino, alkylarylamino, and the like. In addition, substituted aryl groups include tetrafluorophenyl and pentafluorophenyl. The alkyl groups can be optionally interrupted by one or more heteroatoms selected from the group consisting of oxygen, nitrogen, sulfur, and phosphorous.

The Grignard reagents which can be used in practicing the present invention are compounds having the formula $R_{14}MgX$ where $R_{14}$ is as defined above and X is a halogen atom. The halogen atoms which are useful in practicing this invention include chlorine, bromine, and iodine.

Examples of metal cations which are useful in practicing the present invention include, but are not limited to, Group I alkali metals such as, for example, sodium, lithium, potassium, and the like. The preferred metals are sodium, and potassium.

A preferred form of compound 4 is the compound 4a:

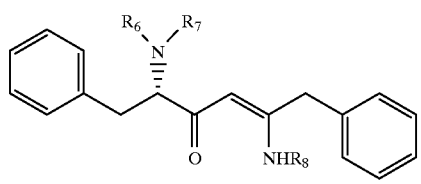

4a where $R_6$ and $R_7$ are independently selected from benzyl and substituted benzyl, wherein the phenyl ring of the benzyl group is substituted with one, two or three substituents independently selected from lower alkyl, trifluoromethyl, alkoxy, halo and phenyl and $R_8$ is hydrogen, benzyl, substituted benzyl, or —C(O)$R_9$ wherein $R_9$ is lower alkyl, alkoxy, or phenyl, wherein the phenyl ring is unsubstituted or substituted with one, two or three substituents independently selected from lower alkyl, trifluoromethyl, alkoxy and halo.

A more preferred form of compound 4a is a compound where $R_6$ and $R_7$ are benzyl and $R_8$ is hydrogen or t-butyloxycarbonyl.

The general process of the invention is illustrated in Scheme I. Protection of the amino group in an L-amino acid and esterification provides compound III. Reaction of III with from about 1.05 to about 1.5 equivalents, preferably from about 1.1 to about 1.3 equivalents, of an α-carbanion of acetonitrile in a suitable solvent provides the enolate-nitrile intermediate II. The reaction is then concentrated and ammonia is removed. Reaction of enolate-nitrile II with about 1.0 to about 3.5 equivalents of Grignard reagent (i.e., $R_{14}$MgX) provides enamine 4. The preferred amount of Grignard reagent is from about 1.25 to about 3.0 equivalents and most preferred is from about 1.5 to about 2.5 equivalents based on the number of equivalents of protected L-amino acid.

SCHEME I

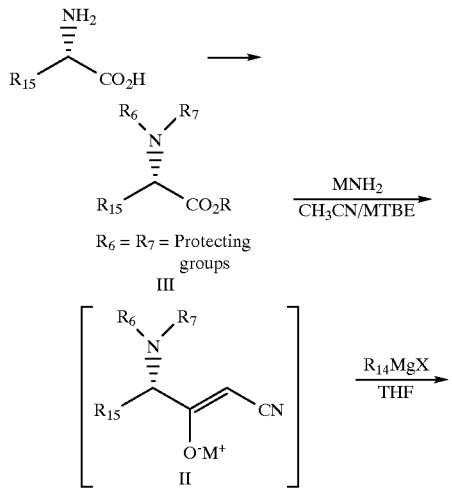

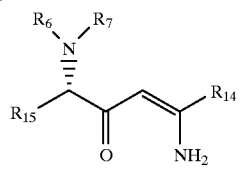

$R_6 = R_7$ = Protecting groups

4

A preferred embodiment for preparing the enamine of the invention having formula 4a is illustrated in Scheme II. The amino group in L-phenylalanine is protected as the dibenzyl amine, and the acid group is simultaneously esterified, i.e., R, $R_6$ and $R_7$ are benzyl, to provide compound 5. Reaction of 5 with the α-carbanion of acetonitrile (about 2.2 equivalents) in an inert solvent, such as, methyl tert-butyl ether (MTBE), provides nitrile-enolate, 6a. Preferably the acetonitrile anion is prepared from sodium or potassium amide (NaNH$_2$ or KNH$_2$). Most preferred is sodium amide. Reaction of the nitrile-enolate, 6a with about 1.5 equivalents of benzyl Grignard (for example, benzyl magnesium chloride) provides enamine, 4a.

The amount of acetonitrile carbanion required is from about 1.0 to about 2.0 equivalents, preferably, from about 1.1 to about 1.5 equivalents. The amount of Grignard reagent required is from about 1.0 to about 3.5 equivalents. The preferred amount of Grignard reagent is from about 1.25 to about 3.0 equivalents and most preferred is from about 1.5 to about 2.5 equivalents, based on the number of equivalents of protected L-amino acid.

Suitable inert solvents for use in the process of the invention include dialkyl ether solvents, such as, for example, methyl ether, ethyl ether, propyl ether, n-butyl ether, methyl n-butyl ether, methyl tert-butyl ether (MTBE), pentyl ether, hexyl ether, dimethoxyethane and the like; a mixture of a solvent such as, for example, tetrahydrofuran (THF), dioxane and the like with an alkyl or cycloalkyl solvent such as, for example, pentane, cyclopentane, hexane, cyclohexane, heptane, and the like. The preferred solvents are the alkyl ethers. A preferred solvent is MTBE.

SCHEME II

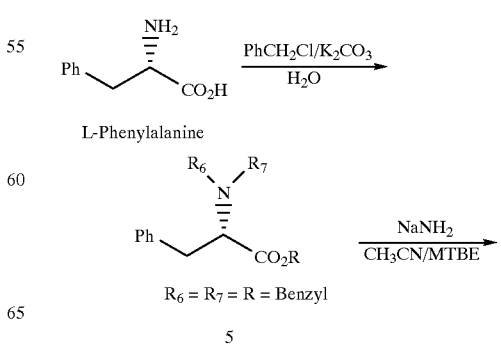

-continued

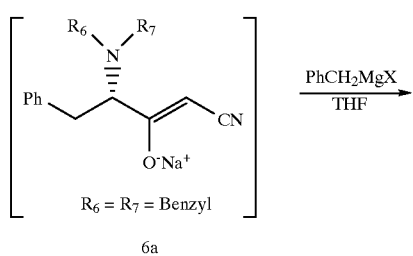

6a

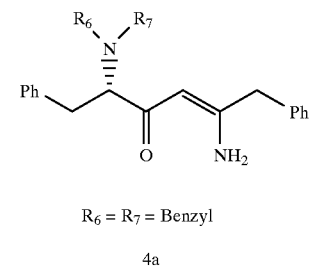

4a

Several processes for the conversion of compounds having formula 4a to the hydroxy-diamine, compounds having formula 3, are disclosed in U.S. Pat. No. 5,354,866, U.S. Pat. No. 5,541,206, and U.S. Pat. No. 5,491,253. The processes for the preparation of compounds having formula 4a disclosed in these patents disclose the purification and isolation of the cyano-ketone 6 prior to conversion to the enamine, 4a. This process is illustrated in Scheme III. The elimination of the additional step of isolating of the nitrile increases the yield by about 20% and reduces the amount of reagents needed to conduct the reaction, particularly the amount of Grignard reagent required, by about 50%.

SCHEME III

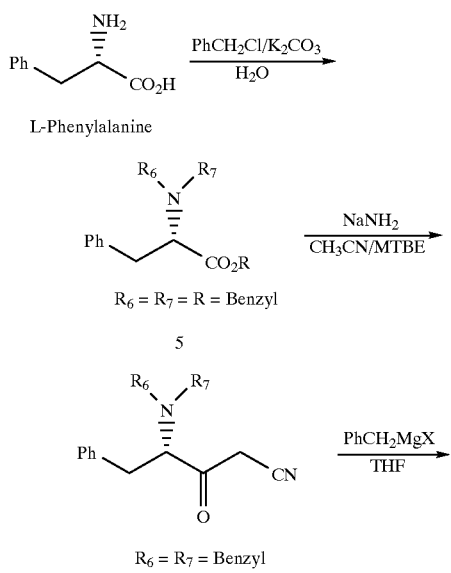

-continued

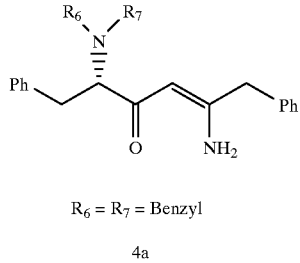

4a

The term "alkyl", as used herein, refers to straight or branched chain alkyl radicals containing from 1 to 12 carbon atoms. The term "lower alkyl" refers to straight or branched chain alkyl radicals containing from 1 to 6 carbon atoms including, but not limited to, methyl, ethyl, n-propyl, iso-propyl, n-butyl, iso-butyl, sec-butyl, t-butyl n-pentyl, 1-methylbutyl, 2,2-dimethylbutyl, 2-methylpentyl, 2,2-dimethylpropyl, n-hexyl, and the like. The alkyl groups can be optionally interrupted by one or more heteroatoms selected from the group consisting of oxygen, nitrogen, sulfur, and phosphorous.

The term "aryl", as used herein, refers to an unsubstituted carbocyclic aromatic radical, including, for example, phenyl and 1- or 2-naphthyl.

The term "cycloalkyl", as used herein, refers to a saturated monocyclic hydrocarbon radicals having from three to eight carbon atoms in the ring and optionally substituted with between one and three additional radicals selected from among alkaryl, alkoxy, loweralkyl, halo, alkylamino, hydroxy-substituted alkyl, hydroxy, alkoxy, halogen, and amino, dialkylamino and the like. Cycloalkyl radicals include, groups such as, for example, cyclopropyl, cyclobutyl, cyclopentyl, cyclohexyl, cycloheptyl, 1-fluorocyclopropyl, 2-fluorocyclopropyl, 2-aminocyclopropyl and the like.

The term "alkoxy" as used herein, refers to groups having the formula —$OR_{10}$ wherein $R_{10}$ is a lower alkyl group.

The term "thioalkoxy" as used herein, refers to groups having the formula —$SR_{11}$ wherein $R_{11}$ is a lower alkyl group.

The term "alkoxyalkoxy" as used herein, refers to groups having the formula —$OR_{16}$—$OR_{10}$ wherein $R_{16}$ is a lower alkylene group $R_{10}$ is a lower alkyl group.

The term "alkaryl" refers to a loweralkyl radical having appended thereto an aromatic hydrocarbon group, as for example benzyl and phenylethyl.

The term "alkylamino" as used herein, refers to groups having the formula —$NHR_{17}$ wherein $R_{17}$ is a lower alkyl group.

The term "dialkylamino" as used herein, refers to groups having the formula —$N(R_{17})_2$ wherein each $R_{17}$ is independently a lower alkyl group.

The term "arylamino" as used herein, refers to groups having the formula —$NHR_{18}$ wherein $R_{18}$ is an aryl group.

The term "diarylamino" as used herein, refers to groups having the formula —$N(R_{18})_2$ wherein each $R_{18}$ is independently an aryl group.

The term "alkylarylamino" as used herein refers to groups having the formula —$N(R_{17}R_{18})_2$ wherein one $R_{17}$ is an alkyl group and the other $R_{18}$ is an aryl group.

The term "halo", as used herein, refers to F, Cl, Br or I.

The term "acid addition salts", as used herein, are salts of an amino group formed with inorganic acids such as hydrochloric acid, hydrobromic acid, phosphoric acid, sulfuric acid perchloric acid, and the like, or with organic acids such as acetic acid, oxalic acid, maleic acid, tartaric acid, citric acid, succinic acid, malonic acid, and the like, or by using other methods used in the art such as ion exchange.

The term "haloalkyl", as used herein, refers to a lower alkyl group in which one or more hydrogen atoms has been replaced with a halogen including, but not limited to, trifluoromethyl, trichloromethyl, difuoromethyl, dichloromethyl, fluoromethyl, chloromethyl, chloroethyl, 2,2-dichloroethyl and the like.

The term "halophenyl", as used herein, refers to a phenyl group in which one, two, three, four or five hydrogen atoms have been replaced with a halogen including, but not limited to, chlorophenyl, bromophenyl, fluorophenyl, iodophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,5-trichlorophenyl, 2,4,6-trichlorophenyl, 2-chloro-4-fluorophenyl, 2-chloro-6-fluorophenyl, 2,4-dichloro-5-fluorophenyl, 2,3-difuorophenyl, 2,4-difuorophenyl, 2,5-difuorophenyl, 2,6-difluorophenyl, 3,4-difuorophenyl, 3,5-difuorophenyl, 2,3,5-trichlorophenyl, 2,4,6-trichlorophenyl, 2,3,4-trifluorophenyl, 2,3,6-trifluorophenyl, 2,4,5-trifluorophenyl, 2,4,6-trifluorophenyl, 3,4,5-trifluorophenyl, 2,3,4,5-tetrafluorophenyl, 2,3,5,6-tetrafluorophenyl, pentafluorophenyl and the like.

The term "lower alkylene" as used herein refers to a divalent group derived from a straight or branched chain saturated hydrocarbon having from 1 to 6 carbon atoms by the removal of two hydrogen atoms, for example methylene (—CH$_2$—), 1,2-ethylene (—CH$_2$CH$_2$—), 1,1-ethylene (=CH—CH$_3$), 1,3-propylene (—CH$_2$CH$_2$CH$_2$—), 2,2-dimethylpropylene (—CH$_2$C(CH$_3$)$_2$CH$_2$—), and the like.

The term "N-protecting group" or "N-protected", as used herein, refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis*, 2nd edition, John Wiley & Sons, New York (1991) N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

As used herein, the terms "S" and "R" configuration are as defined by the IUPAC 1974 Recommendations for Section E, Fundamental Stereochemistry, Pure Appl. Chem. (1976) 45, 13–30.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Me. 01835–9953); Eastman Chemical Company (Rochester, New York 14652–3512); Lancaster Synthesis Inc. (Windham, N.H. 03087–9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

The following examples illustrate the process of the invention, without limitation.

EXAMPLE 1

(L)-N,N-Dibenzylphenylalanine benzyl ester

A solution containing L-phenylalanine (161 kg, 975 moles), potassium carbonate (445 kg, 3220 moles), water (675 L), ethanol (340 L), and benzyl chloride (415 kg, 3275 moles) was heated to 90±15° C. for 10–24 hours. The reaction mixture was cooled to 60° C. and the lower aqueous layer was removed. Heptane (850 L) and water (385 L) were added to the organic layer, stirred, and the layers separated. The organic layer was washed once with a water/methanol mixture (150 L/150 L). The organic layer was removed to provide the title product as an oil. This was carried on in the next step without purification.

Results are illustrated below.

$^1$H NMR (300 MHz, CDCl$_3$)δ 7.5–7.0 (m, 20H), 5.3 (d, 1H, J=13.5 Hz), 5.2 (d, 1H, J=13.5 Hz), 4.0 (d, 2H, J=15 Hz), 3.8 (t, 2H, J=8.4 Hz), 3.6 (d, 2H, J=15 Hz), 3.2 (dd, 1H, J=8.4, 14.4 Hz).

$^{13}$C NMR (300 MHz, CDCl$_3$)δ 172.0, 139.2, 138.0, 135.9, 129.4, 128.6, 128.5, 128.4, 128.2, 128.1, 128.1, 126.9, 126.2, 66.0, 62.3, 54.3, 35.6.

IR (neat) 3090, 3050, 3030, 1730, 1495, 1450, 1160 cm$^{-1}$.

[α]$_D$ −79° (c=0.9, DMF).

EXAMPLE 2

(2S)-5-amino-2-(N,N-dibenzyl)amino-3-oxo-1,6-diphenylhex-4-ene.

A solution comprising (L)-N,N-dibenzyl-phenylalanine benzyl ester (0.24 mole) in 85 mL methyl tert-butyl ether (MTBE) and 13.9 mL, 270 mmole, of acetonitrile was slowly added to a slurry of 90% sodium amide (22.9 g, 0.53 mole) in 185 mL MTBE, keeping the temperature below 0° C. This was stirred for 90 minutes at −5 to 0° C.

The volatile materials were removed, and the reaction volume reduced by about 25%, by vacuum distillation. Benzyl magnesium chloride solution (360 mL; 1M in tetrahydrofuran (THF)) was added to the slurry. The solution was stirred for 6 hours. The excess benzyl magnesium chloride was quenched with a solution of 120 g of citric acid in 630 mL water. The aqueous layer was separated and the organic layer concentrated. The resulting product was crystallized from ethanol to provide 90 g (80%) of (2S)-5-amino-2-(N,N-dibenzyl)amino-3-oxo-1,6-diphenylhex-4-ene (enamine).

Results are illustrated below.

$^1$H NMR (CDCl$_3$) 9.80 (br s, 1H), 7.45–7.05 (m, 20H), 5.10 (s, 1H), 4.90 (br s, 1H), 3.75 (d, J=15Hz, 2H), 3.65 (d, J=15Hz, 2H), 3.55–3.45 (m, 3H), 3.15 (dd J=7.2, 13.2Hz, 1H), 2.97 (dd, J=7.2, 13.2Hz, 1H).

$^{13}$C NMR (CDCl$_3$) 198.2, 162.8, 140.2, 140.1, 135.7, 129.5, 129.3, 128.9, 128.7, 128.1, 128.0, 127.3, 126.7, 125.6, 96.9, 66.5, 54.3, 42.3, 32.4.

IR (film) 3620, 3480, 3030, 1615, 1595, 1520, 1495, 1455 cm$^{-1}$.

MS (Cl) m/e (rel. int.) 461 ((M+H)$^+$, 100), 196 (10).

HPLC ee 100% (Chiracel OD column, 10% iPrOH/Hexanes).

EXAMPLE 3

(2S)-5-Amino-2-(N,N-dibenzyl)amino-3-oxo-1-phenylhex-4-ene

The title compound was prepared from (L)-N,N-dibenzyl-phenylalanine benzyl ester, 46.0 mmole, and 2.6 mL, 50 mmole, of acetonitrile. Following the procedure described in Example 2 the ester and nitrile mixture was added to 4.4 g, 101 mmole of sodium amide in MTBE. Methyl Grignard (CH$_3$MgCl 150 mmole) was substituted for benzyl magnesium chloride. The resulting enamine was crystallized from heptane. The yield of enamine was 17 g (43 mmole, 93%).

Results are illustrated below.

$^1$H NMR (CDCl$_3$); 9.87 (br s,1H, NH), 7.32–7.08 (m, 15H), 5.03 (s, 1H), 5.00 (br s,1H), 3.87 (d, J=13.5Hz, 2H), 3.67 (d, J=13.5Hz, 2H), 3.52 (t, J=7.1Hz, 1H), 3.12 (dd, J=13, 7.1Hz, 1H), 3.01 (dd, J=13, 7.1Hz, 1H), 1.94 (s, 3H).

$^{13}$C NMR (CDCl$_3$); 197.6, 161.1, 140.2, 140.1, 129.5, 128.7, 128.1, 128.0, 126.7, 125.6, 96.7, 66.3, 54.3, 33.1, 22.6.

IR (KBr); 3340, 3260, 3190, 3020, 1620, 1600, 1525, 745, 700 cm$^{-1}$.

HPLC; ee 100% (Chiracel OD column, 10% iPrOH/Hexanes).

EXAMPLE 4

(4S)-1-Amino-4-(N,N-dibenzyl)amino-1,5-diphenyl-3-oxo-pent-1-ene

The title compound was prepared from (L)-N,N-dibenzyl-phenylalanine benzyl ester, 150 mmole, and 8.6 mL, 165 mmole, of acetonitrile. Following the procedure described in Example 2 the ester and nitrile mixture was added to 14.4 g, 330 mmole of sodium amide in MTBE. Phenyl Grignard (PhMgCl 300 mmole) was substituted for benzyl magnesium chloride. The resulting enamine was purified by column chromatography using silica gel, 240/400 mesh and 2:1 heptane/ethyl acetate as the mobile phase. The yield of enamine was 53 g (119 mmole, 79%).

Results are illustrated below.

$^1$H NMR (CDCl$_3$) 10.0 (br s,1H, NH), 7.3 (m, 20H), 5.5 (s, 1H), 5.4 (brs, 1H, NH), 3.95 (d, J=15Hz, 2H),3.8 (d, J=15Hz, 2H), 3.7 (dd, J=7, 8Hz, 1), 3.3 (dd, J=8, 15Hz, 1H), 3.1 (d, J=7, 15Hz).

$^{13}$C NMR (CDCl$_3$) 198.7, 160.9, 140.1, 137.2, 131.0, 129.5, 128.9, 128.7, 128.1, 128.0, 126.7, 126.2, 125.7, 95.8, 66.9, 54.4, 32.8.

IR (film) 3450, 3350, 3070, 3030, 1600, 1560, 1520, 1490, 1450 cm$^{-1}$.

MS (Cl) m/e (rel. int.) 447 (M$^+$, 100), 300 (55).

HPLC ee 97% (Chiracel OD column, 10% i-PrOH/Hexanes).

EXAMPLE 5

4-Amino-1-(N,N-dibenzyl)amino-2-oxo-5-phenyl-pent-3-ene

The title compound was prepared from N,N-dibenzyl-glycine benzyl ester, 54 mmole, and 3.3 mL, 64 mmole of acetonitrile. Following the procedure described in Example 2 the ester and nitrile mixture was added to 5.5 g, 127 mmole of sodium amide in MTBE. After solvent removal, benzyl magnesium chloride (PhCH$_2$MgCl 145 mmole) was added following the procedure in Example 2. The resulting enamine was purified by chromatography, following the procedure described in Example 4. The yield of enamine was 22.3 g (50 mmole, 78%).

Results are illustrated below.

$^1$H NMR (CDCl$_3$);9.8 (brs,1H, NH), 7.3 (m, 15H), 5.6 (s,1H), 5.0 (brs,1H, NH), 3.6 (s, 4H), 3.5 (s, 2H), 3.1 (s, 2H).

$^{13}$C NMR (CDCl$_3$); 198.4, 163.5, 139.2, 135.6, 128.8, 128.7, 128.6, 128.2, 127.3, 126.9, 93.5, 76.6, 62.3, 58.4, 42.2.

IR (Kbr); 3300, 3150, 2810, 1600, 1530, 1580, 1420 cm$^{-1}$.

MS (Cl); m/e (rel. Int.) 371 ((M+H)$^+$, 100), 210 (15).

Elemental Analysis: Calculated for C$_{25}$H$_{26}$N$_2$O: C, 81.1; H, 7.1; N, 7.6; O, 4.3%. Found: C, 81.3; H, 7.1; N, 7.3; O, 4.1%.

EXAMPLE 6

(+)-4-Amino-1-(N,N-dibenzyl)amino-1,5-diphenyl-2-oxo-pent-3-ene

The title compound was prepared from N,N-dibenzyl-glycine benzyl ester, 113 mmole, and 6.5 mL, 125 mmole of acetonitrile. Following the procedure described in Example 2 the ester and nitrile mixture was added to 9.8 g, 225 mmole of sodium amide in MTBE. After solvent removal, benzyl magnesium chloride (PhCH$_2$MgCl 250 mmole) was added following the procedure in Example 2. The resulting enamine was purified by chromatography, following the procedure described in Example 4. The yield of enamine was 41 g (102 mmole, 90%).

Results are illustrated below.

$^1$H NMR (CDCl$_3$); 9.8 (brs, 1H, NH), 7.4 (m, 20H), 5.6 (s, 1H), 5.2 (brs, 1H, NH), 4.5 (s,1H), 3.9 (d, 2H, J=15Hz), 3.7 (d, 2H, J=15Hz), 3.5 (s, 2H).

$^{13}$C NMR (CDCl$_3$); 198.2, 163.9, 140.9, 139.3, 137.5, 135.6, 129.6, 129.1, 128.8, 128.7, 128.3, 128.0, 127.9, 127.3, 127.2, 126.8, 95.02, 71.9, 53.9, 42.1.

IR (film); 3450, 3360, 2970, 2950, 2920, 1610, 1520, 1495, 1450 cm$^{-1}$.

MS (Cl); m/e (rel. int.) 447 (M$^+$, 100), 340 (15), 222(45).

COMPARATIVE EXAMPLE (2S)-5-Amino-2-(N,N-dibenzyl)amino-3-oxo-1,6-diphenylhex-4-ene a. 4-S-N,N-Dibenzylamino-3-oxo-5-phenyl-pentanonitrile.

A solution containing the product of Example 1 (i.e., benzyl ester) (approx. 0.45 moles) in 520 mL tetrahydrofuran and 420 mL acetonitrile was cooled to −40° C. under nitrogen. A second solution containing sodium amide (48.7 g, 1.25 moles) in 850 mL tetrahydrofuran was cooled to −40° C. To the sodium amide solution was slowly added 75 mL acetonitrile and the resulting solution was stirred at −40° C. for more than 15 minutes. The sodium amide/acetonitrile solution was then slowly added to the benzyl ester solution at −40° C. The combined solution was stirred at −40° C. for one hour and then quenched with 1150 mL of a 25% (w/v) citric acid solution. The resulting slurry was warmed to ambient temperature and the organic layer was separated. The organic layer was then washed with 350 mL of a 25% (w/v) sodium chloride solution, then diluted with 900 mL heptane. The organic layer was then washed three times with 900 mL of a 5% (w/v) sodium chloride solution, two times with 900 mL of a 10% methanolic water solution, one time with 900 mL of a 15% methanolic water solution, and then one time with 900 mL of a 20% methanolic water solution. The organic layer was stripped and the resulting material dissolved into 700 mL of hot ethanol. Upon cooling to room temperature, the desired product precipitated. Filtration provided the title product in 59% yield from the L-phenylalanine.

Results are illustrated below.

$^1$H NMR (CDCl$_3$); δ 7.3 (m, 15H), 3.9 (d, 1 H, J=19.5 Hz), 3.8 (d, 2H, J=13.5 Hz), 3.6 (d, 2H, J=13.5 Hz), 3.5 (dd, 1H, J=4.0, 10.5 Hz), 3.2 (dd, 1H, J=10.5, 13.5 Hz), 3.0 (dd, 1H, J=4.0, 13.5 Hz), 3.0 (d, 1H, J=19.5 Hz), $^{13}$C NMR (300 MHz, CDCl$_3$); δ 197.0, 138.4, 138.0, 129.5, 129.0, 128.8, 128.6, 127.8, 126.4, 68.6, 54.8, 30.0, 28.4. [α]$_D$ −95° (c=0.5, DMF).

IR (CHCl$_3$); 3090, 3050, 3030, 2250, 1735, 1600, 1490, 1450, 1370, 1300, 1215 cm$^{-1}$, b. 2-Amino-5-S-N,N-dibenzylamino-4-oxo-1,6-diphenylhex-2-ene To a −5° C. solution of the nitrile product from Comparative Example 2a (90 Kg, 244 moles) in tetrahydrofuran (288 L), was added benzyl magnesium chloride (378 Kg, 2M in THF, 708 moles). The solution was warmed to ambient temperature and stirred until analysis showed no nitrile starting material. The solution was then cooled to 5° C. and slowly transferred to a solution of 15% citric acid (465 kg). Additional tetrahydrofuran (85 L) was used to rinse out the original container and the rinse was added to the citric acid quench container. The organic layer was separated and washed with 10% sodium chloride (235 kg). The solvent was stripped to provide a solid. The crude solid was dissolved in ethanol (289 L) and stripped again. The product was again dissolved in warm (80° C.) ethanol (581 L and cooled to room temperature and stirred for 12 hours. The resulting product was filtered and dried in a vacuum oven at 30° C. to provide the title compound, m.p. 101–102° C., 95 kg, 85% yield, based on N,N-dibenzylphenylalanine benzyl ester.

Results are illustrated below.

$^1$H NMR (300 MHz, CDCl$_3$); d 9.8 (br s, 1H), 7.2 (m, 20H), 5.1 (s, 1H), 4.9 (br s,1H), 3.8 (d, 2H, J=14.7 Hz), 3.6 (d, 2H, J=14.7Hz), 3.5 (m, 3H), 3.2 (dd, 1H, J=7.5, 14.4 Hz), 3.0 (dd, 1H, J=6.6, 14.4 Hz).

$^{13}$C NMR (CDCl$_3$); d 198.0, 162.8, 140.2, 140.1, 136.0, 129.5, 129.3, 128.9, 128.7, 128.1, 128.0, 127.3, 126.7, 125.6, 96.9, 66.5, 54.3, 42.3, 32.4.

IR (CDCl$_3$); 3630, 3500, 3110, 3060, 3030, 2230, 1620, 1595, 1520, 1495, 1450 cm$^{-1}$.

[α]$_D$; −147° (c=0.5, DMF).

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of a compound having formula 4:

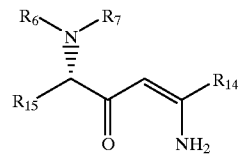

said process comprising:

(a) reacting a compound of the formula:

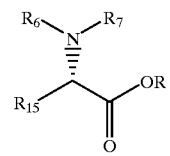

wherein R is C$_1$ to C$_6$ loweralkyl or benzyl, with CH$_3$CN and MNH$_2$ to provide an enolate of the formula:

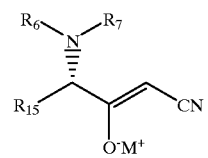

(b) removing the ammonia; and
(c) reacting the resulting ammonia-free enolate with a Grignard reagent having the formula R$_{14}$MgX; wherein
R$_{14}$ is a hydrocarbyl group capable of forming a Grignard reagent selected from the group consisting of alkyl, alkaryl, and aryl;
R$_{15}$ is selected from the group consisting of hydrogen, alkyl, alkaryl, and aryl;
M is an alkali metal ion;
X is a halogen atom selected from the group consisting of chlorine, bromine and iodine; and
R$_6$ and R$_7$ are independently selected from the group consisting of hydrogen, the group:

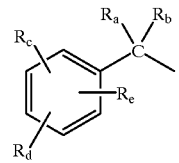

wherein R$_a$ and R$_b$ are independently selected from hydrogen, lower alkyl and phenyl and R$_c$, R$_d$ and R$_e$ are independently selected from hydrogen, lower alkyl, trifluoromethyl, alkoxy, halo and phenyl; and the group:

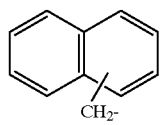

wherein the naphthyl ring is unsubstituted or substituted with one, two or three substitutents independently selected from lower alkyl, trifluoromethyl, alkoxy and halo; or $R_6$ is as defined above and $R_7$ is $R_{12}OC(O)$— wherein $R_{12}$ is benzyl; or $R_6$ and $R_7$ taken together with the nitrogen atom to which they are bonded are

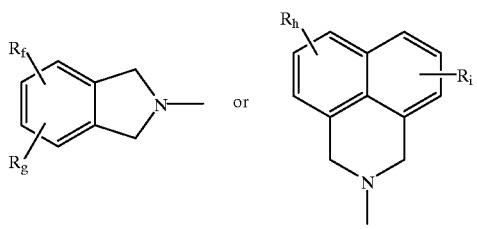

wherein $R_f$, $R_g$, $R_h$ and $R_i$ are independently selected from hydrogen, lower alkyl, alkoxy, halogen and trifluoromethyl with the proviso that $R_6$ and $R_7$ cannot both be hydrogen.

2. The process according to claim 1, wherein $R_{14}$ and $R_{15}$ are independently alkyl, benzyl or phenyl.

3. The process according to claim 2, wherein $R_6$ and $R_7$ are each benzyl.

4. The process according to claim 2, wherein $R_{14}$ and $R_{15}$ are independently methyl, benzyl or phenyl.

5. The process according to claim 4, wherein $R_6$ and $R_7$ are each benzyl.

6. The process according to claim 4, wherein $R_{14}$ and $R_{15}$ are independently benzyl or phenyl.

7. The process according to claim 6, wherein $R_6$ and $R_7$ are each benzyl.

8. The process according to claim 6, wherein $R_{14}$ and $R_{15}$ are each benzyl.

9. The process according to claim 8, wherein $R_6$ and $R_7$ are each benzyl.

10. The process according to claim 4, wherein $R_{14}$ is methyl and $R_{15}$ is benzyl.

11. The process according to claim 10, wherein $R_6$ and $R_7$ are each benzyl.

12. The process according to claim 6, wherein $R_{14}$ is phenyl and $R_{15}$ is benzyl.

13. The process according to claim 12, wherein $R_6$ and $R_7$ are each benzyl.

14. The process according to claim 4, wherein $R_{14}$ is phenyl and $R_{15}$ is methyl.

15. The process according to claim 14, wherein $R_6$ and $R_7$ are each benzyl.

16. The process according to claim 1, wherein $R_{14}$ is benzyl and $R_{15}$ is phenyl.

17. The process according to claim 1, wherein $R_6$ and $R_7$ are each benzyl.

18. The process according to claim 1, wherein the metal ion is selected from the group consisting of sodium, potassium and lithium.

19. The process according to claim 18, wherein the metal ion is sodium.

20. A process for the preparation of a compound having formula 4:

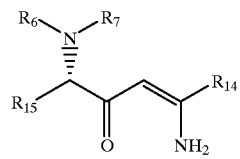

said process comprising (a) reacting a compound of the formula:

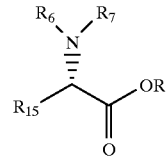

wherein R is benzyl, with $CH_3CN$ and $MNH_2$ wherein M is sodium, lithium or potassium to provide an enolate of the formula:

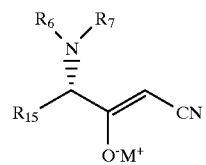

(b) removing the ammonia; and (c) reacting the resulting ammonia-free enolate having the formula:

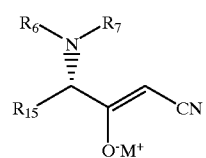

with a Grignard reagent having the formula $R_{14}MgX$;

wherein $R_{14}$ is a hydrocarbyl group capable of forming a Grignard reagent selected from the group consisting of alkyl, alkaryl, and aryl;

$R_{15}$ is selected from the group consisting of hydrogen, alkyl, alkaryl, and aryl;

M is an alkali metal ion; and

X is a halogen atom selected from the group consisting of chlorine, bromine and iodine;

wherein $R_6$ and $R_7$ are independently selected from the group consisting of hydrogen, the group:

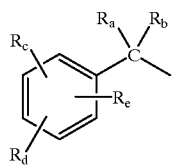

wherein $R_a$ and $R_b$ are independently selected from hydrogen, lower alkyl and phenyl and $R_c$, $R_d$ and $R_e$ are independently selected from hydrogen, lower alkyl, trifluoromethyl, alkoxy, halo and phenyl; and the group:

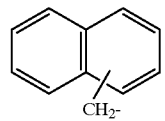

wherein the naphthyl ring is unsubstituted or substituted with one, two or three substitutents independently selected from lower alkyl, trifluoromethyl, alkoxy and halo; or $R_6$ is as defined above and $R_7$ is $R_{12}OC(O)$— wherein $R_{12}$ is benzyl; or $R_6$ and $R_7$ taken together with the nitrogen atom to which they are bonded are

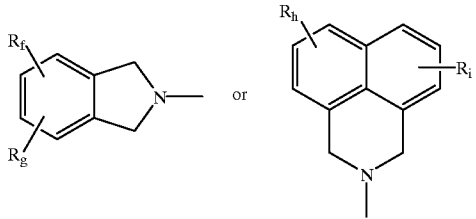

wherein $R_f$, $R_g$, $R_h$ and $R_i$ are independently selected from hydrogen, lower alkyl, alkoxy, halogen and trifluoromethyl with the proviso that $R_6$ and $R_7$ cannot both be hydrogen.

21. The process of claim 20 wherein $R_{14}$ and $R_{15}$ are independently alkyl, phenyl or benzyl, $R_6$ and $R_7$ are benzyl and M is sodium.

22. The process of claim 20 wherein $R_{14}$ and $R_{15}$ are benzyl, $R_6$ and $R_7$ are benzyl and M is sodium.

* * * * *